United States Patent [19]
Scott

[11] Patent Number: 4,562,724
[45] Date of Patent: Jan. 7, 1986

[54] GAS SAMPLING VALVE

[75] Inventor: Richard L. Scott, Bartlesville, Okla.

[73] Assignee: Phillips Petroleum Company, Bartlesville, Okla.

[21] Appl. No.: 628,065

[22] Filed: Jul. 5, 1984

[51] Int. Cl.$^4$ ............................................. G01N 31/08
[52] U.S. Cl. .................................. 73/23.1; 73/863.73; 73/864.83; 137/253; 251/12
[58] Field of Search ............... 73/23.1, 863.71, 863.72, 73/863.73, 864.81, 864.83; 137/247.29, 247.31, 247.27, 247.41, 247.47, 251, 252, 253, 254; 251/12

[56] References Cited
U.S. PATENT DOCUMENTS

| 2,588,214 | 3/1952 | Dawson | 137/253 |
| 2,712,399 | 7/1955 | Blears | 137/253 |
| 2,834,366 | 1/1957 | Bond | 137/251 |
| 3,170,631 | 1/1963 | Whitlow | 137/251 |
| 3,481,205 | 10/1966 | Schmidlin | 73/515 |
| 3,492,873 | 2/1970 | Broerman et al. | 251/62 |
| 3,511,080 | 5/1970 | Roof | 73/23.1 |
| 3,633,426 | 1/1972 | Broerman | 251/62 |

Primary Examiner—Stephen A. Kreitman
Attorney, Agent, or Firm—L. M. Lavin

[57] ABSTRACT

A multi-port, fluid-activated valve mechanism in which positive pressures of control fluids are used to sequentially actuate fluids which seal respective valve ports sequentially. Fritted glass and liquid metals impervious to fritted glass are used as valving means.

6 Claims, 3 Drawing Figures

GAS SAMPLING VALVE

This invention relates to gas sampling valves. It further relates to the use of fritted glass or sintered glass and a liquid such as mercury in a multiport fluid actuated sampling valving means.

It is well known in the art that due to the physical characteristics of liquid metals, such as mercury, particularly its surface tension prevents the liquid metal from flowing through the apertures in fritted glass. On the other hand most liquids with lower surface tension and most gases do pass through the apertures in sintered glass. This knowledge has been used previously in the prior art to create one way valves in which the liquid mercury prevents fluids from passing through the mercury and then through the fritted glass but allows fluid to pass first through the fritted glass and then through the mercury, providing sufficient pressure is used in the latter case.

Gas chromatography is a known method of analyzing fluid samples by preferential sorption and desorption. The desirability of using chromatography for such specific uses as fractionation (multi-stage distillation) control has been recognized for some time. Certain features of process chromatography, such as specific measurement, high sensitivity, and simplicity of operation make this type of analyzer very attractive for use in automatic process control. There are, however, some apparently inherent features of chromatography which have appeared to be obstacles in adapting chromatography to wide-spread use in process control.

One problem that occurs when an attempt is made to use a sampling valve in a gas or liquid stream is maintaining a seal by the moving plunger of the valve.

In U.S. Pat. No. 3,140,615, Arthur B. Broerman, hereby incorporated by reference, there is disclosed and claimed a similar fluid-actuated, multi piston-operated, sampling valve which can be used for chromatographic analysis. This valve is operable up to about 300 p.s.i. very satisfactorily. However, at higher pressures, the sample gas pressure overcomes the force of the springs in the bottom part of the valve and unseals the plungers during the operation, causing leakage from one cavity to the next within the valve.

It has been proposed to overcome the force of the sample gas on the plungers by supplying fluid pressure to the pistons in addition to that supplied by the bottom springs. Due to the construction of the device, the fluid pressure also flows to the upper spring chamber and to the diaphragm seal. This pressure causes sealing in the areas in which the pistons are not in sealing engagement with the diaphragm due to the fact that the carrier gas is at 30 p.s.i. and at that pressure it is not sufficient to overcome the force of the pressure on the underside of the diaphragm. Thus, applying pressure to the spring piston chambers causes improper flow of carrier gas to the sampling valve.

It is an object of this invention to provide a chromatographic analyzer sampling valve sealable by metal fluids which can be used to sample fluid using a carrier fluid.

It is another object of this invention to provide a fluid-actuated sampling valve for supplying sample slugs of a fluid stream to the columns of a chromatographic analyzer with a fluid carrier.

It is a still further object of this invention to provide a fluid-actuated valve for a chromatographic analyzer wherein a liquid metal maintains sealing contact without loss and leaking of the fluid streams are controlled thereby.

Another object of this invention is to provide a valving means that does not wear out over time.

Other aspects, objects, and several advantages of this invention are apparent to one skilled in the art from a study of this disclosure.

SUMMARY OF THE INVENTION

According to the instant invention a sample valve utilizing the impervious property of mercury through fritted glass is used as a valving and sealing means in conjunction with an analyzer.

DETAILED DESCRIPTION OF THE INVENTION

Figure 1:
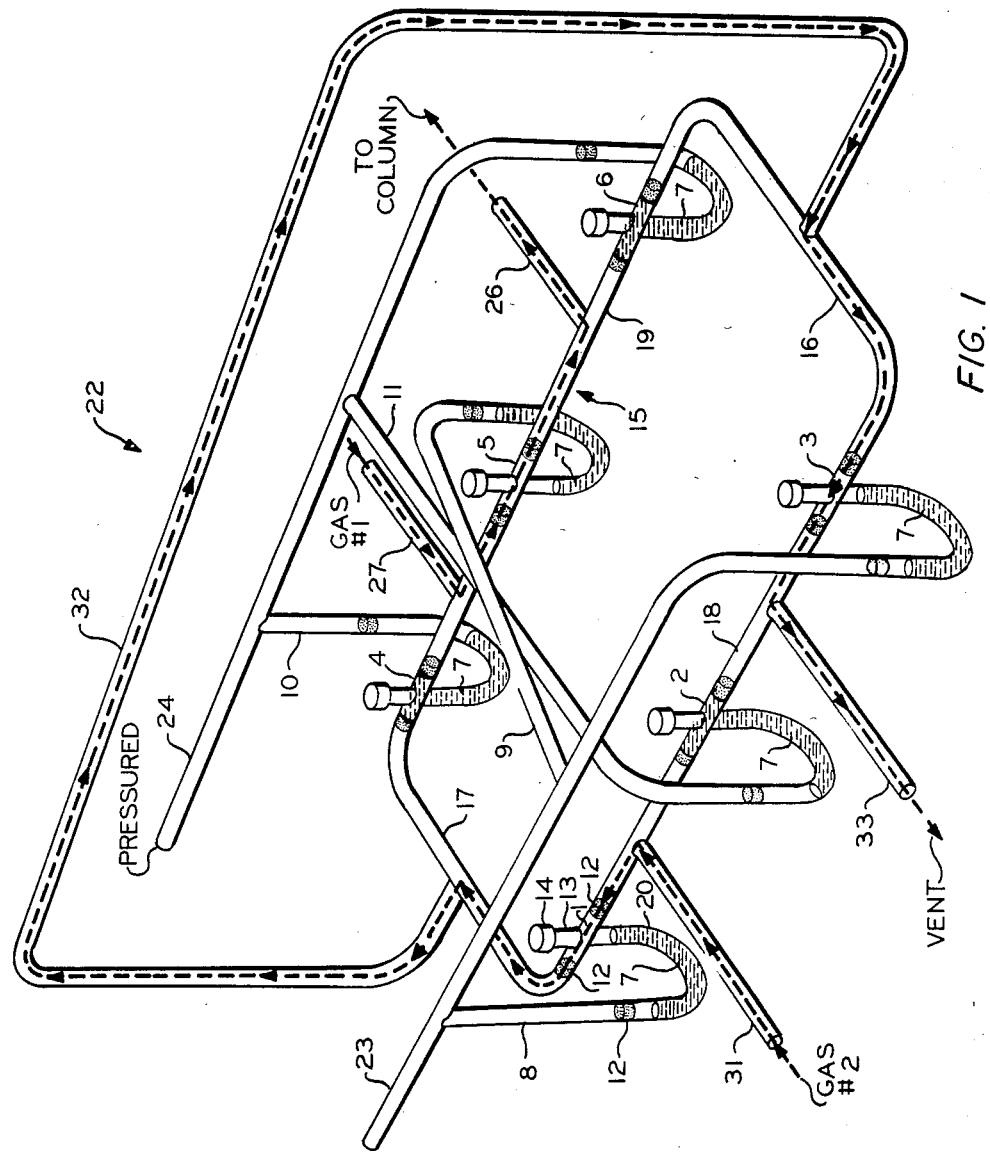
FIG. 1 is a pictorial illustration of the valve in a first position.
Figure 2:
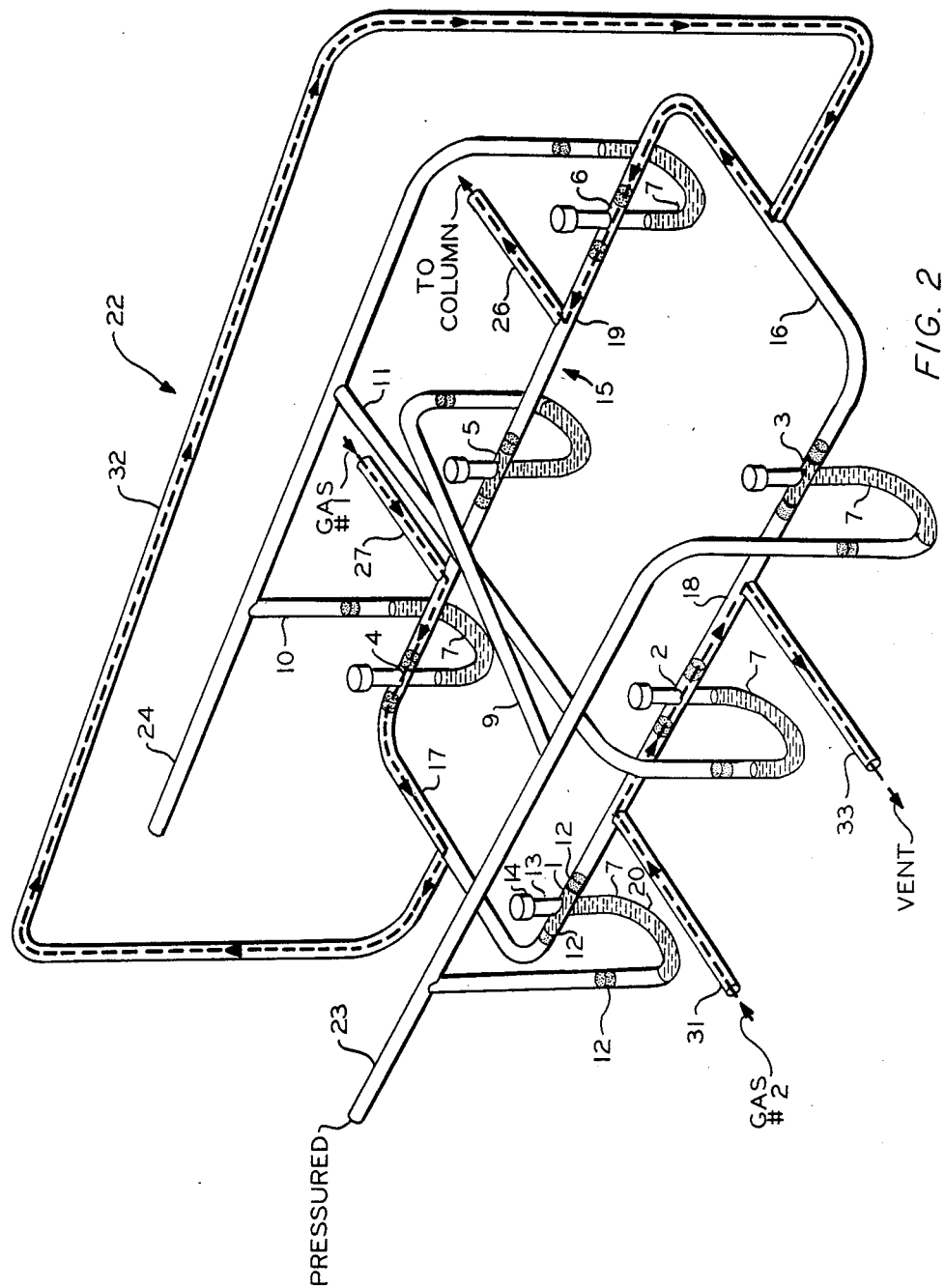
FIG. 2 is a pictorial illustration of the valve in a second position.

Now referring to FIG. 1, valve 22 is a six-port loop conduit having ports 1, 2 and 3 located on side 18 of loop 15 and ports 4, 5 and 6 located on side 19 of loop 15. Sample loop 32 connects ends 17 and 16 of loop 15. Pilot conduits 23 and 24 are provided for shifting the valve through the positions shown in FIG. 1 and FIG. 2 as will be later described. Conduit 27 is provided for a carrier gas such as gas #1 which is to be supplied to the valve and through conduit 26 to a column such as in a gas chromatograph. Conduit 31 is provided for a sample gas #2 entering the valve which can vent from conduit 33 depending on the position of the valve. Conduit 23 is connected to port 1 through branch 8, to port 5 through branch 9, and directly to port 3. Conduit 24 is connected to port 4 through branch 10, to port 2 through branch 11, and directly to port 6. Below each port 1, 2, 3, 4, 5, and 6 the conduit is in a U-shape configuration 20 containing a fluid 7 such as mercury for closing or opening the ports 1–6 depending on pneumatic pressure provided through conduits 23 and 24. A porous material 12 such as a glass frit is provided at the outlets of each port and at the opposite end of U-shape configuration 20 for blocking the fluid 7 such as mercury in the position shown in FIGS. 1 and 2. Conduit extension 13 at each port is provided with a cap 14 which can be a screw type or otherwise sealable cap which can be removed for supplying the mercury to the valve.

The fluid actuated valve 22 can be made from various materials such as glass, metal, Monel, or stainless steel depending on the application and operation of the valve. In the application shown in FIG. 3, the valve conduits are made from stainless steel. Glass frit 12 is of a medium porosity and can also be made from sintered metal, a ceramic, or a capillary bundle in a porosity that will not allow the passage of the mercury through the pores. Gas #1 or the carrier gas can be an inert gas such as nitrogen, helium, hydrogen or argon. The gases used for controlling the valve through conduits 24 can be helium, oxygen, carbon dioxide, water vapor, carbon monoxide, nitrogen, hydrogen, methane, ethylene and the like. The gases used therein should not be reactive with mercury.

Now referring again to FIGS. 1 and 2 in the position shown in FIG. 1 enough pressure is provided through conduit 24 to move the mercury 7 in U-shape configurations 20 upward to close ports 2, 4 and 6 so that carrier gas #1 in conduit 27 passes through port 5 through conduit 26 to a chromatograph column. Gas #2 entering conduit 31 then passes through port 1 and sample loop 32 through port 3 and vents through conduit 33. In the position shown in FIG. 2 enough pressure is provided through conduit 23 to move the mercury 7 in U-shape configurations 20 closing ports 1, 3 and 5 so that gas #1 passes through port 4 and through sample loop 32 and then through port 6 to the chromatograph column. Gas #2 passes through conduit 31 and through port 2 and out conduit 33 to vent.

Figure 3:
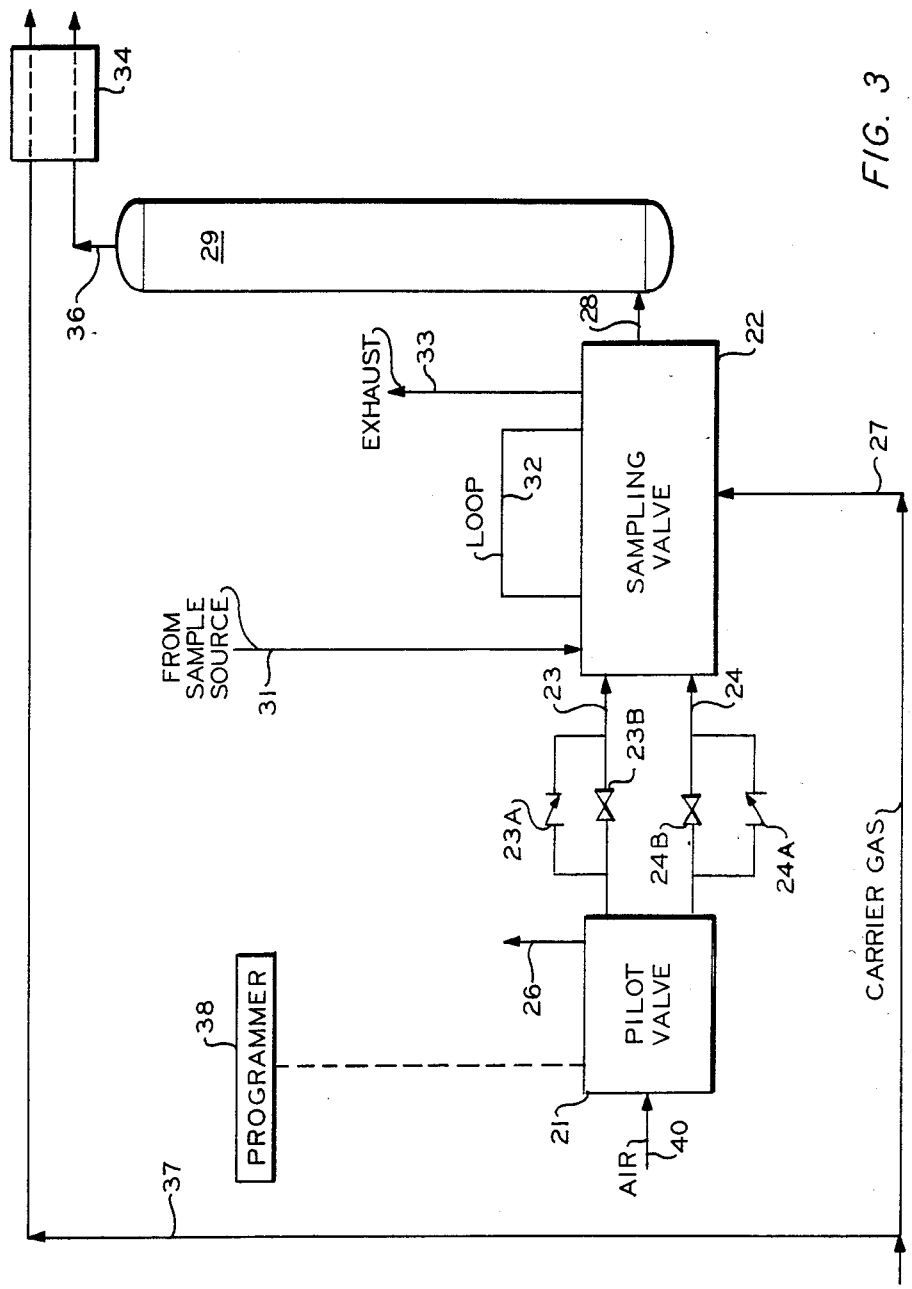
FIG. 3 is a schematic of an adaptation of the valve to chromatographic analysis.

Now referring to FIG. 3 wherein a typical application of fluid activated valve 22 is shown, a gas such as air is supplied by a conduit 40 to pilot valve 21 and is directed to valve 22 via conduit 24 and one-way valve 24A during a first time interval. Conduit 23 is vented through line 23, restrictor 23B, valve 21, line 26. Restrictor 23B substantially prevents the line 23 from venting until full signal pressure is built in line 24. The build up of pressure in line 24 closes ports 2, 4 and 6 as previously described. During a second interval of time gas passes through line 40, pilot valve 21 and conduit 23 and one-way valve 23A to supply pressure on the mercury beneath the ports 1, 3 and 5 activate their closing. During this second interval of time the pressure in conduit 24 is vented through restrictor 24B, pilot valve 21 and pilot exhaust conduit 26. Restrictor 24B substantially prevents a conduit 24 from venting until full signal pressure is built up in conduit 23. Valve 21 can be any suitable four-way valve or can be a combination of two or more three-way valves. When conduit 24 is pressurized as heretofore described, carrier gas #1 is passed via a conduit 27 through port 5 and conduit 26 to chromatograph column 29 allowing gas #2 from a sample source not shown to pass through conduit 31, valve port 1, sample loop 32, through valve port 3, and to vent or exhaust through conduit 33. Periodically as directed by programmer 38 through pilot valve 21, conduit 23 is pressurized as heretofore described to shift the valve closing ports 1, 3 and 5 and opening ports 2, 4 and 6 so that gas #1 or carrier fluid is circulated through port 4 and through sample loop 32 to pick up constituents of the sample gas, then passing through port 6 and conduit 26 to chromatographic column 29 and conduit 36 to detector 34 as known in the art. Detector 34 can be analyzer such as a thermo conductivity assembly. The output signal from the detector 34 is passed to a recording instrument (not shown) which can be a conventional strip chart recorder. A stream of carrier fluid is passed via conduit 37 from conduit 27 directly to the reference cell detector 34 so as to balance out the effect of the carrier fluid in the column 29 effluent. Sample gas #2 to be analyzed generally enters the system continuously through conduit 31. It is exhausted through conduit 33, even when a slug thereof is selected for analysis. Pilot valve 21 is actuated by programmer 38, which can be operated by time cycle or other means as is known in the art.

The application of the valve 22 previously described is not intended to limit its use. It can be used in other applications wherein a fluid activated valve is required. It can also have more or less ports to provide the specific needs of an application.

I claim:

1. A sampling valve comprising multiple ports from a loop conduit, between each port and within said loop conduit is positioned a medium porosity glass-frit disc, where every other port is connected to and in open communication with a conduit containing metal fluid which is further connected to means for injecting said metal fluid into said loop conduit to provide a valving means.

2. A sampling valve as in claim 1 where there is further a sample loop, joining to said loop conduit at opposite ends of said conduit and in open communication with said conduit, where further the same number of remaining parts are on each side of said sample loop in said loop conduit.

3. A sample valve as in claim 1 where said metal fluid is mercury.

4. A sample valve as in claim 2 where there is further joined to said loop conduit pairs of inlet/outlet conduits, each individually located between a valving means where said inlet/outlet conduits and said valving means work cooperatively to provide, through said sample loop, a fluid sample to a analyzing means.

5. A sample valve as in claim 4 where said analyzing means is a chromatographic analyzer.

6. A gas sampling valve utilizing means pervious to gas but impervious to metal fluids to provide a seal comprising a loop conduit containing an even number of ports, between each port in said loop conduit is positioned said means pervious to gas but impervious to metal fluids, where every other port is connected to and in open communication with a conduit containing metal fluid which is further connected to means for injecting said metal fluid into said loop conduit and where at least two of the remaining of said ports join together to form at least one sample loop in open communication with said loop conduit and where at least two further ports remain to provide inlet and outlet means for said gas.

* * * * *

UNITED STATES PATENT AND TRADEMARK OFFICE
CERTIFICATE OF CORRECTION

PATENT NO. : 4,562,724

DATED : JANUARY 7, 1986

INVENTOR(S) : RICHARD L. SCOTT

It is certified that error appears in the above-identified patent and that said Letters Patent is hereby corrected as shown below:

Claim 2, line 5, delete "parts" and insert ---ports---

Signed and Sealed this

Ninth Day of September 1986

[SEAL]

Attest:

DONALD J. QUIGG

Attesting Officer

Commissioner of Patents and Trademarks